US006837856B2

(12) United States Patent
Fujii et al.

(10) Patent No.: US 6,837,856 B2
(45) Date of Patent: Jan. 4, 2005

(54) ULTRASONIC SEARCH UNIT AND METHOD FOR PRODUCING THE SAME

(75) Inventors: Kiyoshi Fujii, Yokohama (JP); Yasushi Koishihara, Yokohama (JP)

(73) Assignee: Matsushita Electric Industrial Co., Ltd., Osaka (JP)

(*) Notice: Subject to any disclaimer, the term of this patent is extended or adjusted under 35 U.S.C. 154(b) by 258 days.

(21) Appl. No.: 10/137,892

(22) Filed: May 3, 2002

(65) Prior Publication Data

US 2003/0055339 A1 Mar. 20, 2003

(30) Foreign Application Priority Data

Sep. 19, 2001 (JP) ....................................... 2001-285456

(51) Int. Cl.[7] .................................................. A61B 8/14
(52) U.S. Cl. ....................................................... 600/459
(58) Field of Search ......................... 600/437, 441–459; 264/308, 401; 310/313 AD, 333, 311, 367; 349/149; 424/9.51–9.53; 29/334, 327, 335, 25.35

(56) References Cited

U.S. PATENT DOCUMENTS

| | | | | |
|---|---|---|---|---|
| 4,616,152 A | * | 10/1986 | Saito et al. | 310/334 |
| 5,553,035 A | * | 9/1996 | Seyed-Bolorforosh et al. | 367/140 |
| 5,651,365 A | * | 7/1997 | Hanafy et al. | 600/459 |
| 5,655,538 A | * | 8/1997 | Lorraine et al. | 600/459 |

FOREIGN PATENT DOCUMENTS

| | | |
|---|---|---|
| JP | 62-189900 | 8/1987 |
| JP | 5-15530 | 1/1993 |
| JP | 7-12239 | 2/1995 |

OTHER PUBLICATIONS

Revised Medical Ultrasonic Equipment Handbook: edited by Electronic Industries Association of Japan, issued by Corona Publishing Co., Ltd., Apr. 1985, p. 42.

"Laser Stereolithography and Recent Topics of the Application"by Tsuneo Hagiwara, OPTICS, vol. 30, No. 4, Apr. 2001, pp. 248–252.

* cited by examiner

*Primary Examiner*—Ali Imam
(74) *Attorney, Agent, or Firm*—Merchant & Gould P.C.

(57) ABSTRACT

An ultrasonic search unit includes a piezoelectric element for transmitting/receiving an ultrasonic wave, and an acoustic matching layer for transmitting the ultrasonic wave transmitted/received by the piezoelectric element to a subject to be measured, wherein the acoustic matching layer is formed of a cured layer obtained by irradiating a resin for optical forming with laser light. It also may be possible that the acoustic matching layer is formed of a plurality of stacked layers, and different fillers are mixed in the respective layers, whereby the acoustic impedance of the respective layers is changed. A liquid resin for optical forming is supplied to a tank, and is cured to a predetermined shape by irradiation with laser light. Accordingly, an ultrasonic search unit and a method for producing the same are provided, in which an acoustic matching layer with a required thickness is formed with good precision without being bonded, whereby a variation in thickness of adhesive layers, a variation in characteristics caused by air bubbles, and degradation are unlikely to occur.

20 Claims, 6 Drawing Sheets

20
11
4
1
10
12

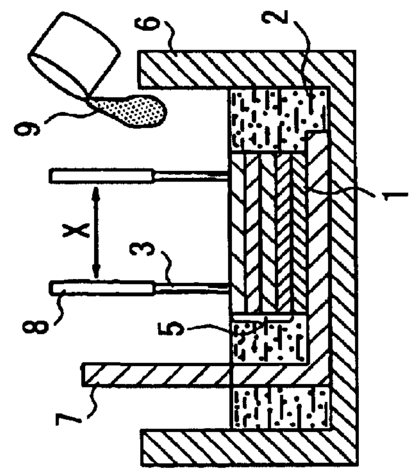
FIG. 6C
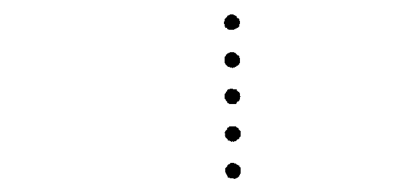
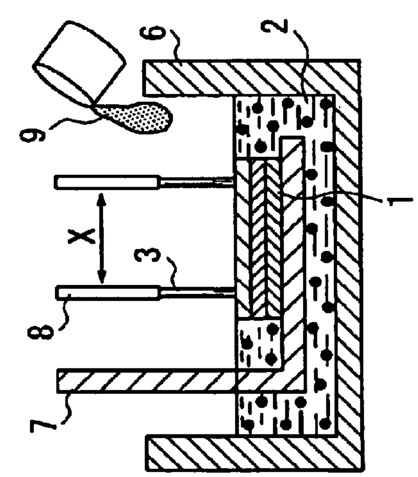
FIG. 6B
FIG. 6A

ULTRASONIC SEARCH UNIT AND METHOD FOR PRODUCING THE SAME

BACKGROUND OF THE INVENTION

1. Field of the Invention

The present invention relates to an ultrasonic search unit used for an ultrasonic diagnostic apparatus that scans an ultrasonic wave electrically or mechanically to display an ultrasonic diagnostic image.

2. Description of the Related Art

Conventionally, regarding an ultrasonic search unit of the abovementioned type, the configuration described in "Revised Medical ultrasonic equipment handbook (p. 42, FIG. 2.39), edited by Electronic Industries Association of Japan, April 1985: issued by Corona Publishing Co., Ltd." is known. Hereinafter, a conventional ultrasonic search unit will be described.

FIGS. 7A and 7B schematically illustrate a configuration of a piezoelectric plate and acoustic matching layers of a conventional ultrasonic search unit and a method for producing the same. A piezoelectric plate 21 shown in FIGS. 7A and 7B converts an electric signal sent from an ultrasonic diagnostic apparatus (not shown) to a mechanical vibration. In order to transmit an ultrasonic signal sent from the piezoelectric plate 21 to a living body as a subject to be measured with good efficiency, a first acoustic matching layer 22 and a second acoustic matching layer 23 are bonded to the front surface of the piezoelectric plate 21 with adhesive layers 24. FIG. 7A shows an exploded view before the first acoustic matching layer 22, the second acoustic matching layer 23, and the piezoelectric plate 21 are bonded to each other. FIG. 7B shows a state where these components are bonded to each other with the adhesive layers 24.

An integrated configuration of the piezoelectric plate 21 and the acoustic matching layers 22 and 23 generally is called an acoustic element. An acoustic element of a conventional ultrasonic search unit converts an electric signal sent from an ultrasonic diagnostic apparatus into a mechanical vibration, using the piezoelectric plate 21. The mechanical vibration of the piezoelectric plate 21 is sent to a human body via the acoustic matching layers 22 and 23. An ultrasonic signal reflected from boundaries of respective tissues in the human body is converted into an electric signal by the piezoelectric plate 21 through a path opposite to that from the piezoelectric plate 21 to the human body. Thus, a tomogram of the human body is displayed on a display screen of the ultrasonic diagnostic apparatus.

JP7(1995)-12239 B describes an ultrasonic search unit using light-curable resin. The invention disclosed therein relates to a method for coating divided groove portions of an array-type ultrasonic search unit with light-curable resin, and does not relate to an acoustic matching layer or a method for producing the same.

JP5(1993)-15530 A describes that a light-curable resin is used as an acoustic matching layer, UV-transparent glass powder is mixed in the resin, and the resin is cured with UV-light.

In the above-mentioned conventional ultrasonic search units, it is difficult to form an acoustic matching layer with a desired thickness, which is made of a material having an acoustic impedance with an intermediate value between the acoustic impedance of the piezoelectric plate and that of the living body, for the purpose of transmitting a vibration of the piezoelectric plate to the living body with good efficiency, More specifically, in the conventional configuration, in order to produce an ultrasonic search unit with a small variation in acoustic characteristics and high acoustic performance, it is required to provide an acoustic matching layer with a desired thickness, which necessitates the management of a treatment operation and a thickness with high precision by polishing or the like. Furthermore, in general, at least one acoustic matching layer previously formed is bonded with an adhesive, and the acoustic matching layer is bonded to the entire surface of the piezoelectric plate with an adhesive. Therefore, even if the acoustic matching layer is treated with high precision, air bubbles in the adhesive layer and a variation in thickness of the adhesive layer may cause a variation in characteristics and degradation of the entire ultrasonic search unit.

SUMMARY OF THE INVENTION

Therefore, with the foregoing in mind, it is an object of the present invention to provide an ultrasonic search unit in which an acoustic matching layer with a required thickness can be formed with good precision without being bonded, whereby a variation in characteristics and degradation of the ultrasonic search unit are unlikely to occur due to the variation in thickness of adhesive layers and the air bubbles mixed in the adhesive layers, and a method for producing the ultrasonic search unit.

It is another object of the present invention to provide an ultrasonic search unit having an acoustic matching layer in which an acoustic impedance can be changed easily from the acoustic impedance of a piezoelectric plate to that of a living body gradually so that a vibration of the piezoelectric plate can be transmitted to the living body with better efficiency.

In order to solve the above-mentioned problem, the ultrasonic search unit of the present invention includes: a piezoelectric element for transmitting/receiving an ultrasonic wave; and an acoustic matching layer for transmitting the ultrasonic wave transmitted/received by the piezoelectric element to a subject to be measured, wherein the acoustic matching layer is formed of a cured layer obtained by irradiating a resin for optical forming with laser light.

The method for producing an ultrasonic search unit including a piezoelectric element for transmitting/receiving an ultrasonic wave and an acoustic matching layer for transmitting the ultrasonic wave to a subject to be measured includes forming the acoustic matching layer by irradiating a liquid resin for optical forming supplied to a tank with laser light to form a cured layer.

These and other advantages of the present invention will become apparent to those skilled in the art upon reading and understanding the following detailed description with reference to the accompanying figures.

BRIEF DESCRIPTION OF THE DRAWINGS

FIGS. 6A to 6C illustrate a method for forming a gradually-changing acoustic matching layer by transferring an ultrasonic search unit of Embodiment 5 according to the present invention to subsequent tanks successively.

DESCRIPTION OF THE PREFERRED EMBODIMENTS

Figure 1A:
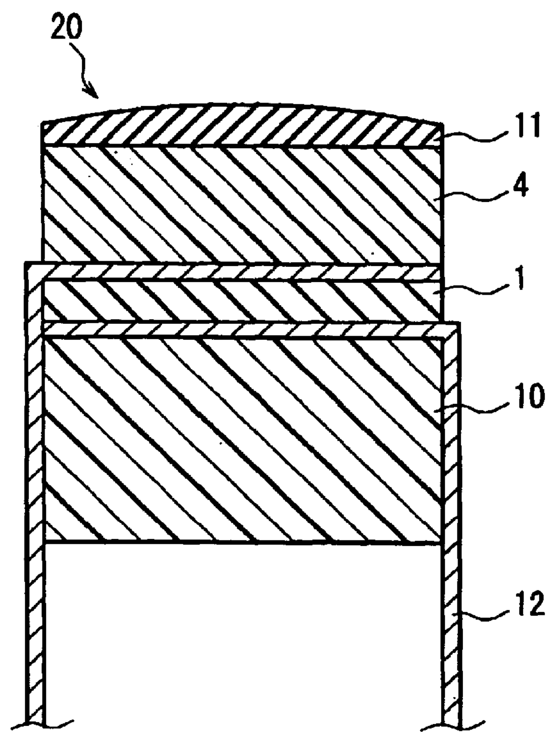
FIG. 1A schematically illustrates an ultrasonic search unit of Embodiment 1 according to the present invention.

According to the present invention, by forming an acoustic matching layer of a cured layer obtained by curing a resin for optical forming with laser light, an acoustic matching layer with a desired thickness, high thickness precision, and less variation in characteristics can be obtained easily.

In the ultrasonic search unit of the present invention, it is preferable that an acoustic matching layer is formed of cured layers of a light-curable resin stacked on a piezoelectric element. According to this configuration, the acoustic matching layer can be formed on the piezoelectric plate without being bonded thereto. Therefore, air bubbles are unlikely to be generated as a result of the use of an adhesive, which enables the acoustic matching layer with less variation in characteristics to be formed easily.

In the ultrasonic search unit of the present invention, it is preferable that the acoustic matching layer is formed with an arbitrary filler mixed in the light-curable resin. According to this configuration, the acoustic matching layer with an appropriate acoustic impedance required for transmitting/receiving an ultrasonic wave with good efficiency can be formed easily.

Furthermore, in the ultrasonic search unit of the present invention, it is preferable that an acoustic impedance in the acoustic matching layer is changed successively in a thickness direction. Because of this, an ultrasonic signal of the piezoelectric plate can be transmitted/received with better efficiency.

Furthermore, in the ultrasonic search unit of the present invention, it is preferable that the acoustic impedance in the acoustic matching layer is changed successively by stacking a plurality of layers having different contents of a filler successively. Because of this, an ultrasonic signal transmitted/received by the piezoelectric plate can be transmitted with good efficiency in accordance with an individual difference or a site of a subject to be measured.

Furthermore, in the ultrasonic search unit of the present invention, it is preferable that the acoustic matching layer is formed of a light-curable resin mixed with a mixture of fillers with at least two different particle sizes or a filler with a particle size changing in a layer direction. Because of this, an acoustic matching layer with an appropriate acoustic impedance required for transmitting/receiving an ultrasonic wave with good efficiency can be formed easily, and an ultrasonic signal of the piezoelectric plate can be transmitted/received with good efficiency.

Furthermore, in the ultrasonic search unit of the present invention, it is preferable that the acoustic matching layer is formed of a light-curable resin mixed with a mixture of fillers with at least two different densities or a filler with a density changing in a layer direction. Because of this, an ultrasonic signal of the piezoelectric plate can be transmitted/received with good efficiency.

Furthermore, in the ultrasonic search unit of the present invention, it is preferable that at least one selected from the group consisting of tungsten, ferrite, and alumina is mixed in the light-curable resin as a filler. Because of this, an acoustic matching layer having an intermediate value of the acoustic impedance of a piezoelectric element and that of a human body can be formed easily, and an ultrasonic signal can be transmitted/received with good efficiency. Herein, ferrite refers to a particular crystal structure of iron (Fe).

Furthermore, according to the method of the present invention, the acoustic matching layer is formed of a cured layer obtained by curing a liquid resin for optical forming supplied to a tank with laser light, thereby curing the resin to a predetermined shape. Because of this, an acoustic matching layer with a desired thickness, high thickness precision, and less characteristics can be obtained easily.

Furthermore it is preferable that a filler in an amount of 0 mass % to 2000 mass % is mixed in the resin.

Furthermore, it is preferable that an amount of a filler in a lower layer is set to be relatively high, and an amount of a filler in a surface layer is set to be relatively low by using a settling speed of the filler mixed in the resin, whereby an acoustic impedance is changed in a thickness direction.

Furthermore, it is preferable that a resin layer constituting the acoustic matching layer is formed of a plurality of layers, a density of the resin layer in a lower layer is set to be high, and a density of the resin layer in a surface layer is set to be low, whereby an acoustic impedance is changed in a thickness direction.

Furthermore, it is preferable that the density of the resin layer is controlled by changing at least one selected from the group consisting of an added amount of a filler, an average particle size thereof, and a density thereof.

According to the present invention, an acoustic matching layer can be formed on a piezoelectric plate without being bonded thereto. Therefore, air bubbles are unlikely to be generated as a result of the use of an adhesive, which enables an acoustic matching layer with less variation in characteristics to be formed easily.

Hereinafter, the present invention will be described by way of illustrative embodiments with reference to the drawings.

Embodiment 1

As shown in FIG. 1A, an ultrasonic search unit 20 of Embodiment 1 according to the present invention includes a piezoelectric plate 1 for transmitting/receiving an ultrasonic wave, an acoustic matching layer (gradually-changing matching layer) 4 for transmitting/receiving an ultrasonic wave with good efficiency, a backing material 10 for holding the piezoelectric plate 1 and suppressing an efficiency loss due to the backward leakage of an ultrasonic wave, an acoustic lens 11 for allowing an ultrasonic wave to converge at any position of a subject (not shown) to be measured with good efficiency, an electrode wiring material 12, a cable (not shown), and a connector (not shown). Among them, the acoustic matching layer 4 is formed by curing a part of a liquid curable resin for optical forming (hereinafter, referred to as a "liquid light-curable resin") by a method generally called optical forming, as described later.

Figure 1B:
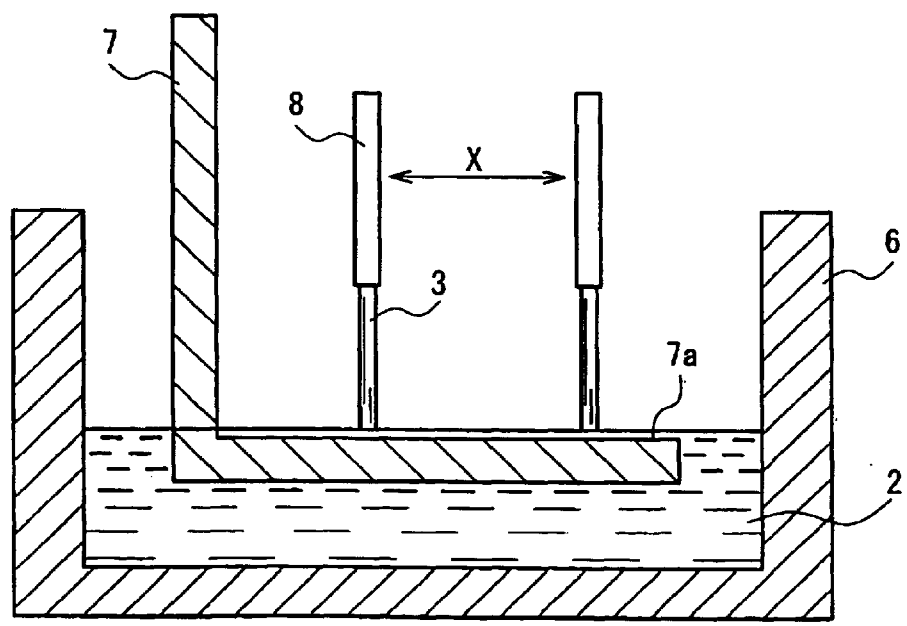
FIG. 1B schematically illustrates a method for forming an acoustic matching layer of the ultrasonic search unit by optical forming.

A method for curing a part of a liquid light-curable resin 2 will be described with reference to FIG. 1B. A tank 6 is filled with the liquid light-curable resin 2. An upper surface (work support surface) 7*a* of a vertical movement platform 7 is lowered from the liquid surface of the liquid light-curable resin 2 by a distance corresponding to a predetermined thickness to be cured. By irradiating laser light hereinafter, referred to as a "laser") 3 such as a UV-laser or an Ar laser emitted from a laser radiator 8 at this position, a site of the liquid light-curable resin 2 irradiated with the laser 3 can be cured.

The laser 3 is radiated to the liquid light-curable resin 2 on the work support surface 7*a* of the vertical movement platform 7 spot-wise or in a wide range under the condition that a region other than a required portion is masked, while an irradiation position is being controlled with an irradiation position control unit (not shown) such as a digital scan mirror or a movement unit (not shown) of the laser radiator 8. Irradiation is conducted for a predetermined period of time, whereby a thin cured layer in a predetermined shape can be formed on the work support surface 7*a* of the vertical movement platform 7.

The thin cured layer is lowered successively by the vertical movement platform 7 at a predetermined speed, and the laser 3 is radiated at a predetermined timing. Layers are stacked successively in this manner to form cured layers with a desired thickness.

Herein, the liquid light-curable resin 2 is composed of a photopolymerizable oligomer, a reactive diluent, a photopolymerization initiator, and the like. The liquid light-curable resin 2 has a property that only a portion irradiated with light is cured, and is mixed with a photopolymerization assistant, an additive, and the like, if required. The photopolymerizable oligomer is classified into those cured by radical polymerization such as a urethane acrylate type, an epoxy acrylate type, an ester acrylate type, and an acrylate type, and those cured by cation polymerization such as an epoxy type and a vinyl ether type. Which type of resin is used is determined based on a reaction speed, contraction strain, size precision, heat resistance, strength, and the like.

In general, a light-curable resin containing a photopolymerizable oligomer of a urethane acrylate type or an epoxy type mainly is used. The urethane acrylate type has a high reaction speed and a large intermolecular cohesion. Therefore, the urethane acrylate type is more advantageous in mechanical strength/thermal strength, and is more preferablee in view of strength, compared with the epoxy type. On the other hand, the epoxy type has a low polymerization reaction speed and small contraction strain. Therefore, the epoxy type is more advantageous in size precision, and is more preferable in view of precision, compared with the urethane acrylate type.

Examples of the epoxy type light-curable resin include "HS-681" (trade name) produced by Asahi Denka Kogyo K.K., "SOMOS 8100" (trade name) produced by DSM-SOMOS (the same product also is available as "SCR-8100 series" from JSR), and "SL-7540" (trade name) produced by Vantico (former Ciba Specialty Chemicals). Furthermore, an example of the urethane acrylate light-curable resin includes "TSR-1938M" (trade name) produced by Teijin Seiki Co., Ltd.

Figure 2:
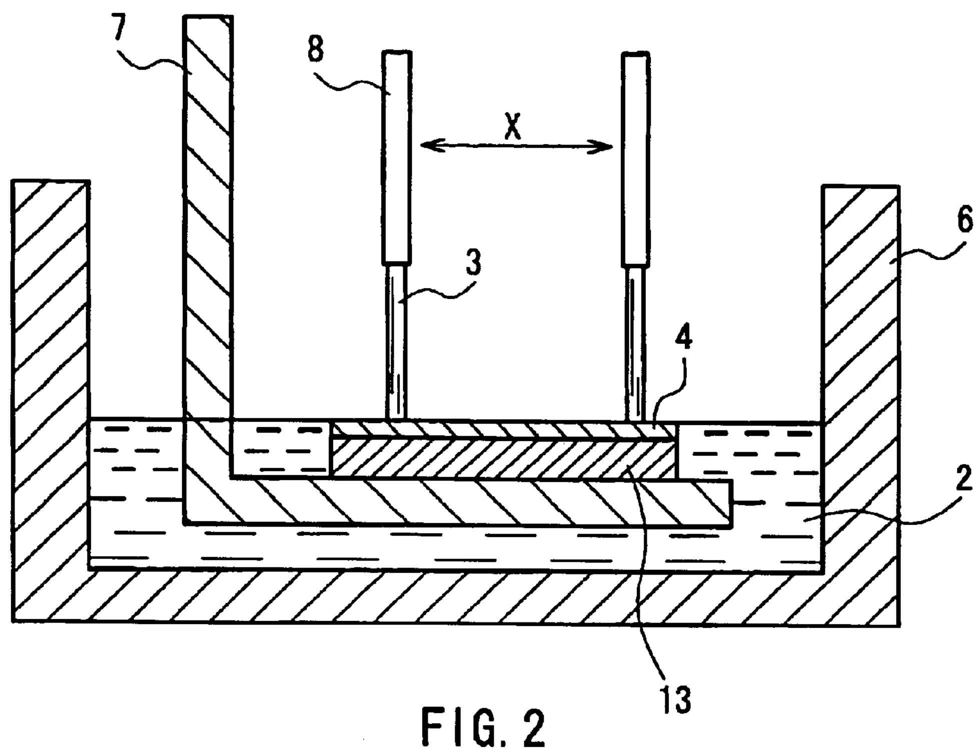
FIG. 2 illustrates a method for forming an acoustic matching layer directly on a piezoelectric plate in Embodiment 1 according to the present invention.

A method for stacking cured layers of a light-curable resin directly on a base plate 13, using a curing unit of the liquid light-curable resin 2 by optical forming will be described with reference to FIG. 2.

First, the base plate 13 fixed on the vertical movement platform 7 is soaked in the liquid curable resin 2 that fills the tank 6. The liquid light-curable resin 2 on an upper portion of the base plate 13 is irradiated with the laser 3 emitted from the laser radiator 8, whereby the liquid light-curable resin 2 on the base plate 13 is cured.

While the laser radiator 8 is moved in parallel with the base plate 13 (in a horizontal direction) based on positional data of an X-Y coordinate or a polar coordinate, the laser 3 is radiated onto the liquid light-curable resin 2 uniformly at a predetermined position, whereby the liquid light-curable resin 2 is cured on the base plate 13 to form a thin acoustic matching layer 4.

Although not shown, the vertical movement platform 7 is lowered by a predetermined distance, and the laser 3 is radiated onto the liquid light-curable resin 2 again, whereby a new cured layer of the liquid light-curable resin 2 can be formed on the thin acoustic matching layer 4 of the light-curable resin 2 that has already been cured. Thus, by controlling the distance by which the vertical movement platform 7 is lowered and repeating the above operation so that the total movement distance of the vertical movement platform 7 becomes a finally required size of the acoustic matching layer 4, the acoustic matching layer 4 with a desired thickness can be formed on the base plate 13.

As described above, in Embodiment 1 of the present invention, the acoustic matching layer 4 can be formed on the base plate 13 without using materials respectively polished to a desired thickness and without using an adhesive.

No adhesive layers 24 are formed between the base plate 13 (i.e., a piezoelectric plate) and the acoustic matching layer 4 in the ultrasonic search unit of Embodiment 1 of the present invention. Therefore, there is no variation (about 2 $\mu$m to 15 $\mu$m) in the thickness of the adhesive layers, which may be caused in a stacking process by conventional general bonding. Furthermore, there is no influence of air bubbles mixed in the adhesive layers 24. As a result, an acoustic matching layer can be formed easily, which has a desired thickness, high thickness precision, and less variation in acoustic characteristics of each acoustic element after being divided by dicing, and a highly reliable ultrasonic search unit can be provided.

Embodiment 2

Next, a method for forming an acoustic matching layer 4 with a changing acoustic impedance will be described with reference to FIG. 3.

Figure 3:
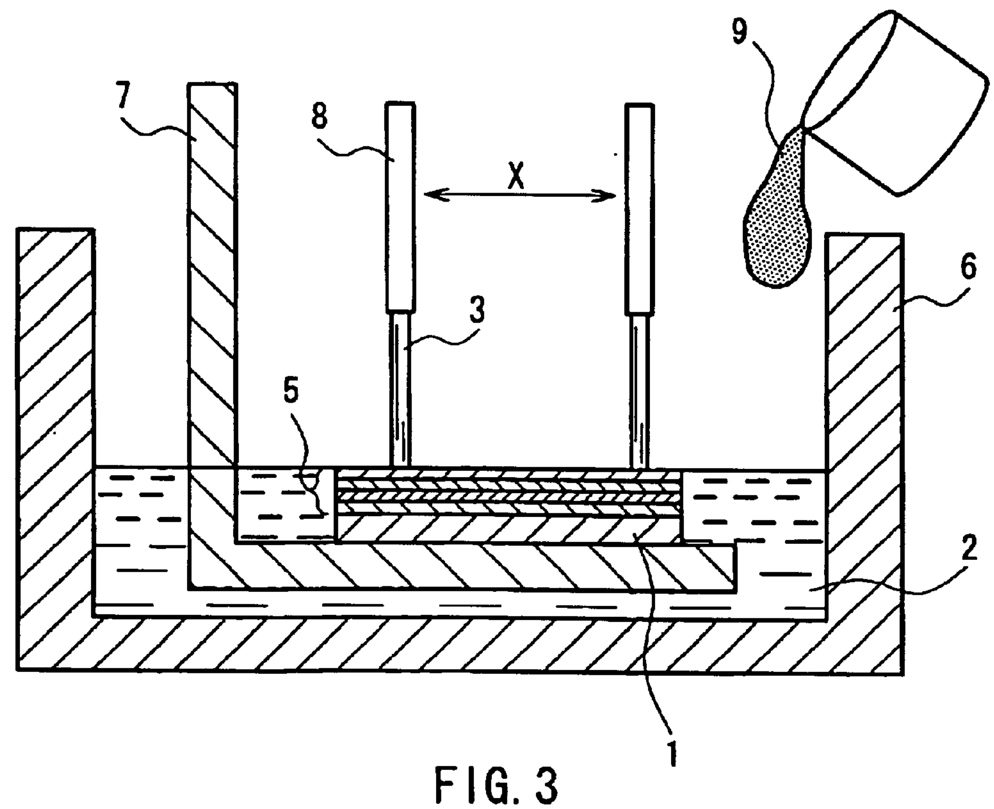
FIG. 3 illustrates a method for forming a gradually-changing acoustic matching layer of an ultrasonic search unit of Embodiment 2 according to the present invention.

As shown in FIG. 3, when cured layers of the liquid light-curable resin 2 are stacked, a filler 9 in a fine powder, fiber, or plate shape is mixed in the liquid light-curable resin 2 in the tank 6, whereby an acoustic matching layer 4 with desired acoustic impedance characteristics can be formed.

The filler 9 is mixed in the liquid light-curable resin 2, and dispersed therein uniformly with a stirrer. Examples of the filler 9 include tungsten, ferrite, and alumina, and an appropriate average particle size thereof is about 1 $\mu$m to 10 $\mu$m.

The acoustic impedance of the acoustic matching layer 4 generally has an intermediate value between the acoustic impedance (about 30 Mrayl) of the piezoelectric plate 1 and that (about 1.5 Mrayl) of the human body. For example, when maintaining the same material and the same particle size for the filler 9, by adjusting the amount of the filler 9 to be mixed in the liquid light-curable resin 2, it is possible to set the acoustic impedance of the acoustic matching layer 4 in the vicinity of an intended value (i.e., from about 30 Mrayl to about 1.5 Mrayl).

Because of this, an acoustic matching layer with a desired thickness, high thickness precision, and less variation in characteristics easily can be formed, and a highly reliable ultrasonic search unit can be provided.

Herein, the collection of a plurality of layers with a gradually-changing acoustic impedance will be referred to as a "gradually-changing matching layer".

Embodiment 3

Next, a method for producing an acoustic matching layer 4 of an ultrasonic search unit of Embodiment 3 according to the present invention will be described with reference to FIGS. 4A to 4C.

Figure 4C:
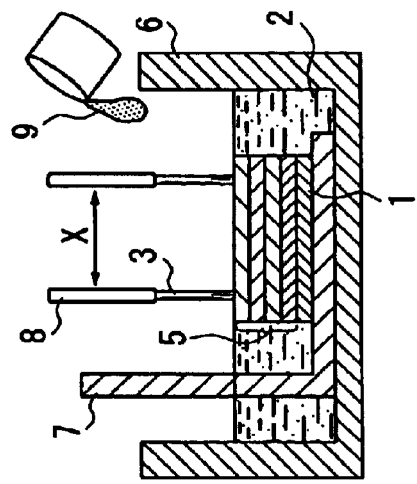
FIGS. 4A to 4C illustrate a method for forming a gradually-changing acoustic matching layer by transferring an ultrasonic search unit of Embodiment 3 according to the present invention to subsequent tanks successively.
Figure 4B:
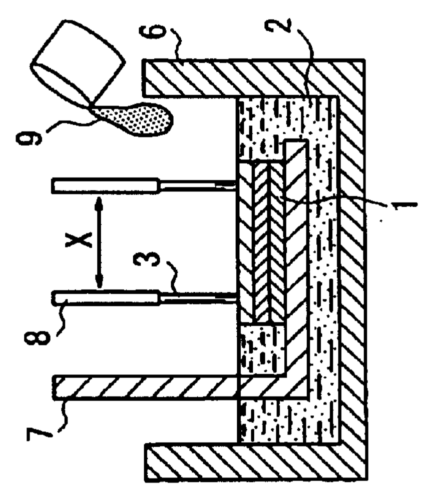
Figure 4A:
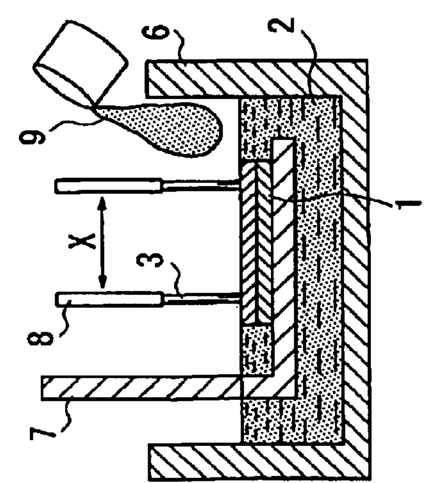

As shown in FIGS. 4A to 4C, in addition to Embodiment 2, when cured layers of the liquid light-curable resin 2 are stacked, the amount (mixed amount) of the filler 9 is changed gradually for each layer to be stacked, using a plurality of tanks 6.

A material having a density larger than that of the liquid light-curable resin 2 is used for the filler 9, and the amount of the filler 9 to be mixed in the liquid light-curable resin 2 is increased gradually, whereby an average density of the entire liquid light-curable resin 2 containing the filler 9 is increased. An acoustic impedance is represented by a product of the density of a material and a sound transmission speed (sonic speed). As is understood from this, with an increase in an average density of the entire liquid light-curable resin 2, the acoustic impedance is increased.

Based on the above, by stacking cured layers of the liquid light-curable resin 2 while changing the mixed amount of the filler 9 gradually, acoustic matching layers 4 with a gradually changing acoustic impedance in a thickness direction can be formed. Thus, by adjusting the amount of the filler 9 to be mixed, it is possible to set the change in acoustic impedance to be any change such as a step-by-step change, a linear change, and a series change, in accordance with a position in a thickness direction.

A specific method for changing the amount of the filler 9 is as follows. The filler 9 is dispersed uniformly in the liquid light-curable resin 2, whereby several kinds of the tanks 6 are prepared in which the filler 9 is mixed and dispersed so as to obtain the desired acoustic impedance, respectively; every time one acoustic matching layer 4 is stacked in each tank 6, the resultant stack is moved (transferred) from the tank 6 containing a larger mixed amount of the filler 9 to the tank 6 containing a smaller mixed amount of the filler 9, and soaked in another tank 6 having a different amount of the filler 9; and another acoustic matching layer 4 is stacked on the previously stacked acoustic matching layer 4, whereby acoustic matching layers 4 with a gradually changing acoustic impedance in a thickness direction can be formed.

As the filler 9 to be mixed, tungsten, ferrite, alumina, and the like can be used, and an average particle size thereof preferably is about 1 $\mu$m to 10 $\mu$m. Hereinafter, the entire acoustic matching layer 4 composed of a plurality of layers in which the acoustic impedance is changed gradually in a thickness direction will be referred to as a "gradually-changing matching layer 5".

The acoustic impedance of the gradually-changing matching layer 5 can be changed gradually from the acoustic impedance of the piezoelectric plate 1 to that of a human body (i.e., a subject to be measured). Therefore, the acoustic impedance is adjusted by changing the amount of the filler 9 gradually so that the acoustic impedance is changed from about 30 Mrayl to about 1.5 Mrayl. More specifically, it is preferable that the gradually-changing matching layer 5 is formed so that the density of a lower layer becomes higher, and the density of an upper layer becomes lower.

At this time, the amount of the filler 9 to be mixed can be changed arbitrarily by a step-by-step change, a linear change, a series change, or the like, in accordance with a distance in a thickness direction. An ultrasonic signal to be transmitted/received by the piezoelectric plate 1 can be transmitted with good efficiency in accordance with an individual difference or a site of a subject to be measured.

Embodiment 4

Next, a method for producing an acoustic matching layer 4 of an ultrasonic search unit of Embodiment 4 according to the present invention will be described with reference to FIGS. 5A to 5C.

Figure 5C:
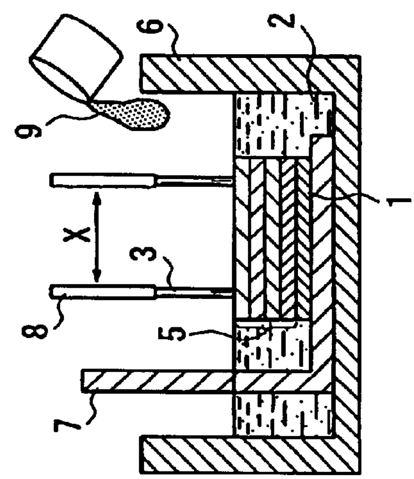
FIGS. 5A to 5C illustrate a method for forming a gradually-changing acoustic matching layer by transferring an ultrasonic search unit of Embodiment 4 according to the present invention to subsequent tanks successively.
Figure 5B:
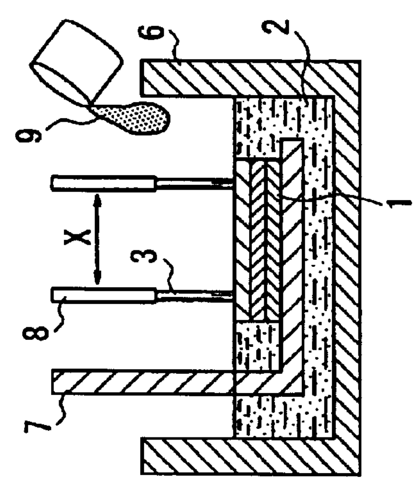
Figure 5A:
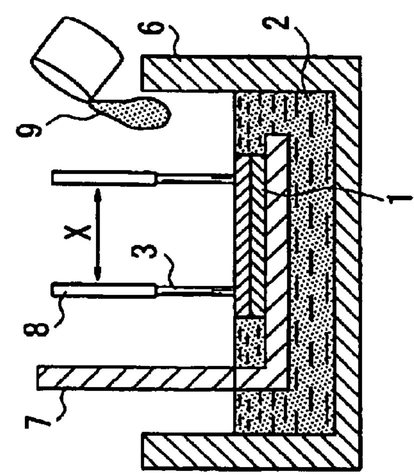
Figure 7A:
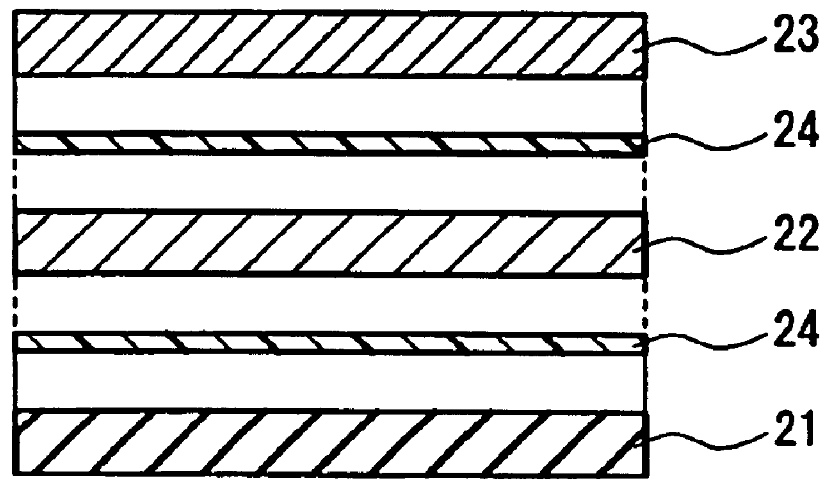
FIG. 7A is an exploded view illustrating the state before conventional acoustic matching layers are bonded.
Figure 7B:
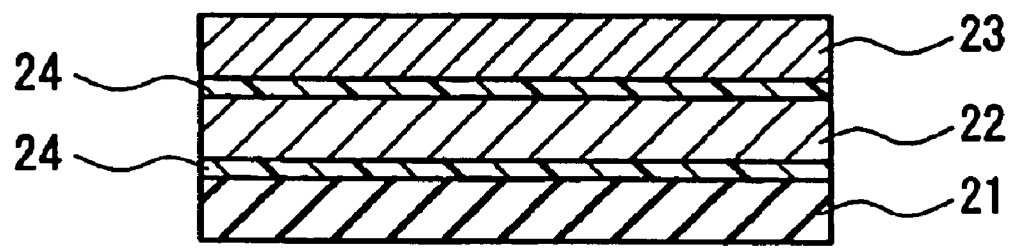
FIG. 7B illustrates a bonded state of the conventional acoustic matching layers.

As shown in FIGS. 5A to 5C, in addition to Embodiment 1, when cured layers of the liquid light-curable resin 2 are stacked, the density of the filler 9 is changed, whereby an average density of the entire liquid light-curable resin 2 is changed. As a result, acoustic matching layers 4 with a gradually changing acoustic impedance in the thickness direction can be formed.

As the filler 9, tungsten (19.3 g/cm$^3$), ferrite (7.015 g/cm$^3$), alumina (3.95 g/cm$^3$) and the like are used in a decreasing order of the density. However, other materials may be used.

A specific method for changing an average density of the entire liquid light-curable resin 2 using the above-mentioned fillers is as follows. As described in Embodiment 2, several kinds of the tanks 6 are prepared; the fillers 9 with different densities are mixed and stirred in the liquid light-curable resins 2 in the respective tanks 6; and acoustic matching layers 4 are stacked and cured successively in the respective tanks 6, whereby a gradually-changing matching layer 5 can be formed.

In the case of using tungsten, ferrite, and alumina as the filler 9, tungsten is mixed and stirred in the liquid light-curable resin 2 in a first tank 6, ferrite is mixed and stirred in the liquid light-curable resin 2 in a second tank, and alumina is mixed and stirred in the liquid light-curable resin 2 in a third tank. Acoustic matching layers 4 are stacked successively from the first tank 6 having a larger density material for the filler 9. As a result, the acoustic impedance of the acoustic matching layers 4 can be changed gradually from a large value to a small value. Thus, the acoustic impedance of the gradually-changing matching layer 5 is changed gradually from the acoustic impedance of the piezoelectric plate 1 to that of a human body. For this purpose, the fillers 9 with different densities are mixed in the liquid light-curable resins 2 so that an acoustic impedance is changed from about 30 Mrayl to about 1.5 Mrayl in a stacking thickness direction, thereby adjusting an acoustic impedance.

Furthermore, when the fillers having the same particle size and different densities are mixed simultaneously in the liquid light-curable resin 2, the settling speed of the filler 9 with a large density is higher than that of the filler 9 with a small density. Therefore, in the case where such a liquid light-curable resin 2 is left for a predetermined period of time, the filler 9 with a large density is present in a deep portion of the liquid light-curable resin 2, and the filler with a small density is present in a shallow portion thereof. As a result, a state where the density of the filler 9 is changed in a depth direction can be obtained. By curing the liquid light-curable resin 2 in this state, the gradually-changing matching layer 5 can be formed using one tank 6.

Embodiment 5

A method for producing the acoustic matching layer 4 of Embodiment 5 according to the present invention will be described with reference to FIGS. 6A to 6C.

As shown in FIGS. 6A to 6C, in addition to Embodiment 1, when cured layers of the liquid light-curable resin 2 are stacked, the particle size of the filler 9 is changed, whereby the acoustic matching layers 4 are formed in which an acoustic impedance is changed in a thickness direction in the same way as in the above. Even if the material of the filler 9 is the same, by changing a particle size thereof, the entire gravity (or weight) of the liquid light-curable resin 2 with the filler 9 mixed therein is changed, whereby the acoustic impedance can be changed.

Thus, an acoustic matching layer can be formed easily with an appropriate acoustic impedance (changing gradually from an acoustic impedance of the piezoelectric plate 1 to that of a human body) required for efficiently transmitting/receiving an ultrasonic wave, and an ultrasonic signal of the piezoelectric plate 1 can be transmitted/received efficiently.

A specific method for changing a particle size of the filler 9 is as follows. Several kinds of the tanks 6 are prepared, which contain the liquid light-curable resins 2 with the fillers 9 having different particle sizes mixed and stirred therein; one layer is stacked for each tank 6, whereby a gradually-changing matching layer 5 is formed by a stacking process. As the filler 9, any of the above-mentioned materials or other materials may be used. An average particle size of the filler 9 generally is about 1 to 10 μm. If required, a particle size larger than this range may be used.

In the present embodiment, acoustic matching layers 4 with a gradually changing acoustic impedance also can be stacked using one tank 6. More specifically, the filler 9 in a weight ratio of 5% is mixed and stirred in the liquid light-curable resin 2, and a first layer is cured. Then, before a second layer is cured, the filler 9 in a weight ratio of 5% further is added and stirred, and the second layer is cured. This procedure is repeated, whereby acoustic matching layers 4 with a gradually changing acoustic impedance can be stacked using one tank 6.

It also is possible to combine the respective Embodiments 2 to 5. In this case, the acoustic impedance can be changed more minutely.

Furthermore, instead of stacking the acoustic matching layers 4 of the light-curable resin 2 directly on the piezoelectric plate 1, it also may be possible that the acoustic matching layer 4 is formed singly, and bonded to the piezoelectric plate 1 to form an ultrasonic search unit.

In the above-mentioned embodiments, the acoustic matching layers 4 on the piezoelectric plate 1 have an acoustic impedance gradually changing from the acoustic impedance of the piezoelectric plate 1 to that of a living body. Therefore, the acoustic matching layers 4 with a gradually changing acoustic impedance in a thickness direction can be formed, which cannot be realized by a conventional method for bonding the respective acoustic matching layers 4. As a result, an ideal acoustic matching layer can be realized.

The present invention will be described more specifically below.

EXAMPLE 1

As light-curable resin, "TSR-820" resin (trade name) produced by Teijin Seiki Co., Ltd was used. In a first tank, tungsten powder with an average particle size of 13 μm in an amount of 1385 mass % was mixed with "TSR-820" resin. In a second tank, tungsten powder with a particle size of 3 to 5 μm in an amount of 400 mass % was mixed with "TSR-820" resin. In a third tank, only "TSR-820" resin was used.

As laser light, a semiconductor solid laser (wavelength: 355 nm) was used. A laser irradiation power was set to be 500 mW, a laser light scanning speed was set to be 2 m/sec., and an irradiation area was set to be 250 $mm^2$. The thickness of a layer obtained by one scanning was set to be 100 μm.

Under the above condition, a first layer was formed using the resin solution in the first tank, a second layer was formed using the resin solution in the second tank, and a third layer was formed using the resin solution in the third tank. As a result, gradually-changing stacked matching layers with a total thickness of 300 μm (each layer having a thickness of 100 μm) were formed.

The characteristics of the resultant gradually-changing stacked matching layers were as follows. The acoustic impedance of the first layer was Z=17 Mrayl, that of the second layer was Z=7.7 Mrayl, and that of the third layer was Z=2.8 Mrayl. It was confirmed that matching layers were formed in which the acoustic impedance was changed gradually from the acoustic impedance (about 30 Mrayl) of a piezoelectric plate to that (about 1.5 Mrayl) of a human body.

In the case where one matching layer was bonded by a conventional method, the characteristics of a piezoelectric element, e.g., a specific band at a −6 dB position (a ratio (fw/f) of a frequency bandwidth "fw" at a −6 dB position from a gain of a central frequency "f" of an ultrasonic signal transmitted from the piezoelectric plate, with respect to the central frequency "f") was 50%, whereas the specific band of a piezoelectric element in which three matching layers were formed according to the present invention was substantially 100%. Thus, according to the present invention, a piezoelectric element with a large band was obtained (in the case of two layers, a specific band was 60%).

Furthermore, in a subsequent stage, a piezoelectric element including such acoustic matching layers was provided with grooves in a thickness direction to be divided into a plurality of small pieces in a slice shape, and an electrode was connected to each small piece. At this time, the variation in characteristics of each small piece (divided element) may have a large effect on the characteristics of the entire ultrasonic search unit. However, unlike the conventional example, in the ultrasonic search unit obtained by the method of the present invention, it is not required to bond the acoustic matching layers with an adhesive. Therefore, the acoustic matching layers having high precision were formed, in which there was no variation in thickness precision of adhesive layers and no variation caused by air bubbles in the entire element as well as in each piece (divided element).

As described above, according to the present invention, a variation in band characteristics, frequency characteristics such as a shift of a central frequency, and a variation in sensitivity were suppressed to a half or lower of the conventional example.

Thus, in the ultrasonic search unit of the present invention, acoustic matching layers can be formed easily with a desired thickness, high thickness precision, and less variation in characteristics, and an ultrasonic search unit with high acoustic performance can be provided.

The invention may be embodied in other forms without departing from the spirit or essential characteristics thereof. The embodiments disclosed in this application are to be considered in all respects as illustrative and not limiting. The scope of the invention is indicated by the appended claims rather than by the foregoing description, and all changes which come within the meaning and range of equivalency of the claims are intended to be embraced therein.

What is claimed is:

1. An ultrasonic search unit, comprising:

a piezoelectric element for transmitting/receiving an ultrasonic wave; and an acoustic matching layer for transmitting the ultrasonic wave transmitted/received by the piezoelectric element to a subject to be measured, wherein the acoustic matching layer is formed of a cured layer obtained by irradiating a resin for optical forming with laser light, and wherein the acoustic matching layer is formed directly on the piezoelectric element.

2. An ultrasonic search unit according to claim 1, wherein the acoustic matching layer is stacked on the piezoelectric element.

3. An ultrasonic search unit according to claim 1, wherein the acoustic matching layer is formed with a filler in an amount of 0 mass % to 2000 mass % mixed in the resin.

4. An ultrasonic search unit according to claim 3, wherein the filler has at least two different average particle sizes.

5. An ultrasonic search unit according to claim 3, wherein the filler has at least two different densities.

6. An ultrasonic search unit according to claim 3, wherein the filler is at least one selected from the group consisting of tungsten, ferrite, and alumina.

7. An ultrasonic search unit according to claim 3, wherein the acoustic matching layer is formed of a plurality of layers, a ream composition of a lower layer has a relatively high density, and a resin composition of a surface layer has a relatively low density.

8. An ultrasonic search unit according to claim 1, wherein the acoustic matching layer has an acoustic impedance that changes in a thickness direction.

9. An ultrasonic search unit according to claim 8, wherein the acoustic matching layer is formed of a plurality of layers, a lower layer thereof has a relatively high acoustic impedance, and a surface layer thereof has a relatively low acoustic impedance.

10. An ultrasonic search unit according to claim 8, wherein the acoustic matching layer includes a plurality of stacked layers in which a content of a filler is change between adjacent layers.

11. An ultrasonic search unit according to claim 1, wherein the acoustic matching layer is formed of a plurality of layers, and there is no adhesive layer between the layers.

12. An ultrasonic search unit according to claim 1, wherein the acoustic matching layer is formed of a plurality of layers, and there are no air bubbles between the layers.

13. A method for producing an ultrasonic search unit including a piezoelectric element for transmitting/receiving an ultrasonic wave and an acoustic matching layer for transmitting the ultrasonic wave to a subject to be measured, the method comprising forming the acoustic matching layer directly on the piezoelectric element by irradiating a liquid resin for optical forming supplied to a tank with laser light to form a cured layer.

14. A method for producing an ultrasonic search unit according to claim 13, wherein a filler in an amount of 0 mass % to 2000 mass % is mixed in the resin.

15. A method for producing an ultrasonic search unit according to claim 13, wherein an amount of a filler in a lower layer is set to be relatively high, and an amount of a filler in a surface layer is set to be relatively low by using a settling speed of the filler mixed in the resin, whereby an acoustic impedance is changed in a thickness direction.

16. A method for producing an ultrasonic search unit according to claim 13, wherein a resin layer constituting the acoustic matching layer is formed of a plurality of layers, a density of the resin layer in a lower layer is set to be relatively high, and a density of the resin layer in a surface layer is set to be relatively low, whereby an acoustic impedance is changed in a thickness direction.

17. A method for producing an ultrasonic search unit according to claim 13, wherein the density of the resin layer is controlled by changing at least one selected from the group consisting of an added amount of a filler, an average particle size thereof, and a density thereof.

18. A method for producing an ultrasonic search unit according to claim 13, wherein the filler is at least one selected from the group consisting of tungsten, ferrite, and alumina.

19. A method for producing an ultrasonic search unit according to claim 13, wherein the acoustic matching layer is formed of a plurality of layers, and there is no adhesive layer between the layers.

20. A method for producing an ultrasonic search unit according to claim 13, wherein the acoustic matching layer is formed of a plurality of layers, and there are no air bubbles between the layers.

* * * * *